United States Patent
Urynowicz et al.

(10) Patent No.: US 10,151,185 B2
(45) Date of Patent: Dec. 11, 2018

(54) BIOMASS-ENHANCED NATURAL GAS FROM COAL FORMATIONS

(75) Inventors: Michael A. Urynowicz, Fort Collins, CO (US); Song Jin, Fort Collins, CO (US)

(73) Assignee: University of Wyoming, Laramie, WY (US)

( * ) Notice: Subject to any disclaimer, the term of this patent is extended or adjusted under 35 U.S.C. 154(b) by 656 days.

(21) Appl. No.: 13/437,689

(22) Filed: Apr. 2, 2012

(65) Prior Publication Data

US 2013/0092370 A1 Apr. 18, 2013

Related U.S. Application Data

(60) Provisional application No. 61/470,351, filed on Mar. 31, 2011.

(51) Int. Cl.
| | |
|---|---|
| *C12N 1/20* | (2006.01) |
| *C12P 5/02* | (2006.01) |
| *C12P 5/00* | (2006.01) |
| *E21B 43/16* | (2006.01) |
| *E21B 43/00* | (2006.01) |

(52) U.S. Cl.
CPC ............ *E21B 43/16* (2013.01); *C12N 1/20* (2013.01); *C12P 5/023* (2013.01); *E21B 43/006* (2013.01); *Y02E 50/343* (2013.01)

(58) Field of Classification Search
CPC ............................ C12P 5/023; Y02E 50/343
See application file for complete search history.

(56) References Cited

U.S. PATENT DOCUMENTS

| | | | |
|---|---|---|---|
| 5,501,273 A | 3/1996 | Puri | |
| 7,556,094 B1 | 7/2009 | Urynowicz et al. | |
| 7,640,978 B2 * | 1/2010 | Pfeiffer et al. | 166/246 |
| 2001/0045279 A1 | 11/2001 | Converse et al. | |
| 2007/0248531 A1 * | 10/2007 | Debryun et al. | 423/650 |
| 2007/0251146 A1 | 11/2007 | Larter et al. | |
| 2009/0246849 A1 * | 10/2009 | Jin | B09B 3/00 435/167 |
| 2010/0047793 A1 | 2/2010 | Toledo et al. | |
| 2010/0081184 A1 * | 4/2010 | Downey et al. | 435/167 |
| 2010/0093046 A1 | 4/2010 | Remmereit et al. | |
| 2010/0101782 A1 | 4/2010 | Pfeiffer et al. | |
| 2011/0027849 A1 | 2/2011 | Jin et al. | |
| 2011/0308790 A1 * | 12/2011 | Strapoc et al. | 166/250.01 |

FOREIGN PATENT DOCUMENTS

| | | |
|---|---|---|
| CA | 2691094 A1 | 12/2008 |
| CN | 102383771 A | 3/2012 |

OTHER PUBLICATIONS

White "Bioconversion of brewer's spent grains to bioethanol" FEMS Yeast Res 8 (2008) 1175-1184.*
International Search Report, International Searching Authority, dated Jun. 27, 2012, pp. 1-14.
Canadian Examination Report for Patent Application No. 2,831,902, dated Apr. 6, 2018, six total pages.

* cited by examiner

*Primary Examiner* — Louise Humphrey
*Assistant Examiner* — Charles Zoltan Constantine
(74) *Attorney, Agent, or Firm* — Samuel M. Freund; Cochran Freund & Young LLC

(57) ABSTRACT

The use of coal fields as subsurface bioreactors for producing sustainable methane gas from terrestrial sources of biomass is described. Microbial presence is determined for a target coal formation, and tracers are injected to determine permeability, porosity, volume, and minimum and a maximum material injection rates. At least one injection well and at least one circulation well effective for generating an injection rate between the minimum and maximum injection rates are provided for injecting a solution of biodegradable materials into the coal seam. A chosen quantity of biodegradable materials is allowed to be digested, fermented and converted by microbial action within the coal seam. Methane gas is extracted through producing and injecting wells, although pumping will enhance gas recovery.

30 Claims, 3 Drawing Sheets

BIOMASS-ENHANCED NATURAL GAS FROM COAL FORMATIONS

CROSS-REFERENCE TO RELATED APPLICATIONS

The present application claims the benefit of U.S. Provisional Patent Application No. 61/470,351 for "Biomass-Enhanced Natural Gas From Coal Formations," which was filed on 31 Mar. 2011, the entire contents of which is hereby specifically incorporated by reference herein for all that it discloses and teaches.

STATEMENT REGARDING FEDERAL RIGHTS

This invention was made with government support under Contract No. RPSEA 07122-14 awarded by the Research Partnership to Secure Energy for America. The government has certain rights in the invention.

BACKGROUND

The United States has the world's largest coal reserves estimated at 6 trillion tons, and coal is the nation's most abundant fossil fuel resource. Unfortunately, 90 percent of the coal is un-mineable due to seam thickness, depth, and structural integrity. One way that the nation's substantial un-mineable coal resources can produce energy is through the extraction of coal bed natural gas (CBNG) which is primarily methane (coal-bed methane (CBM)) absorbed on coal surfaces and held in place by the hydrostatic pressure exerted by groundwater. Water is pumped out of the seam to the surface through wells that are screened along the coal seam in order to release the pressure, which eventually allows the methane to desorb from the coal surface for extraction. Unlike coal, CBM is clean-burning and its recovery requires minimal surface disruption. For the sub-bituminous coal that is produced in the Powder River Basin (PRB) of Wyoming and Montana, there are 200,000 lb of $CO_2$, 2,800 lb of particulates, and 0.02 lb of mercury produced per billion BTU of energy output. By comparison, natural gas produces 100,000 lb of $CO_2$, 7 lb of particulates, and 0 lb of mercury. Constituents causing acid rain such as sulfur dioxide and nitrogen oxide are also significantly reduced. Natural gas costs, on average, are more than one-third lower than conventional gas at the pump, and natural gas has been 25-42 percent less expensive than diesel over the last 14 years. Natural gas is also used as the hydrogen source for many fuel cells, and burning natural gas heats the majority of homes in the U.S.

The estimated total CBNG within the PRB, located in Wyoming and Montana, is 39 trillion cubic feet (TCF), of which about 90% is located in the Wyoming portion of the basin. In the early 1990's, several small CBNG companies began producing natural gas and produced water from coal seams located within the PBR. To date, there have been nearly 30,000 wells drilled in the PRB. CBNG has constituted a significant proportion of the total U.S. production of natural gas over the past two decades, with annual production increasing to 1.8 TCF or approximately 9% of total production.

The principal constituent in CBNG is methane (sometimes referred to as coal bed methane ((CBM)), with trace levels of propane, butane, $N_2$, and $O_2$. Extraction requires a significant capital investment in gas-collection and water-management infrastructure, including extraction wells, separators, compressors, pipelines, outfalls, and evaporation ponds, but the average operational life of a CBNG well is less than 8 years. Consequently, much of the infrastructure used for CBNG production is decommissioned or abandoned as coal beds become depleted, which represents a significant loss with respect to capital expenditures, existing infrastructure, and inefficient use of resources.

SUMMARY

Embodiments of the present invention overcome the disadvantages and limitations of the prior art by providing a method for generating secondary biogenic natural gas in underground coal formations.

It is further an object of embodiments of the present invention to provide a method for generating sustainable biogenic natural gas in underground coal formations.

Another object of embodiments of the present invention is to provide a method for generating sustainable natural gas in underground coal formations using existing coal bed methane infrastructure.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method for generating methane gas hereof, includes the steps of: selecting a coal seam; determining microbial presence of the chosen coal seam; injecting tracers into the chosen coal seam to determine permeability, porosity, and minimum and maximum material injection rates; providing at least one injection well and at least one circulation well effective for generating an injection rate between the minimum and maximum injection rates; removing formation water; mixing a solution of soluble biodegradable materials with the removed formation water and injecting the solution formed thereby into the coal seam; permitting a chosen quantity of the biodegradable materials to be digested or fermented by microbial action in the coal seam, whereby methane gas is generated; and extracting the methane gas from the coal seam.

In another aspect of the present invention and in accordance with its objects and purposes, the method for generating methane gas hereof, includes the steps of: introducing a solution of biodegradable materials into a coal bed; permitting a chosen quantity of the biodegradable materials to be digested or fermented by anaerobic bacteria in the coal bed, whereby methane gas is generated; and extracting the methane gas from the coal bed.

In yet another aspect of the present invention and in accordance with its objects and purposes, the method for generating methane gas hereof, includes the steps of: removing a portion of the formation water from a methanogenically active coal bed; extracting the methane gas desorbed from the coal bed; introducing a solution of biodegradable materials into the coal bed; permitting a chosen quantity of the biodegradable materials to be digested or fermented by anaerobic bacteria in the coal bed, whereby methane gas is generated; and extracting the natural gas from the coal bed.

Benefits and advantages of embodiments of the present invention include, but are not limited to, providing a method for generating new natural gas in coal seams from terrestrial biodegradable materials, wherein the coal, having a natural affinity for methane, acts as a sink, thereby storing the generated natural gas until it can be economically recovered. Advantages of the present method further include increasing the biogenic conversion of coal and coal-derived compounds to natural gas by increasing the population and activity of microorganisms in the coal seam responsible for the production of secondary biogenic coal bed natural gas. Further, embodiments of the invention permit recycling of otherwise unusable biomass.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1:
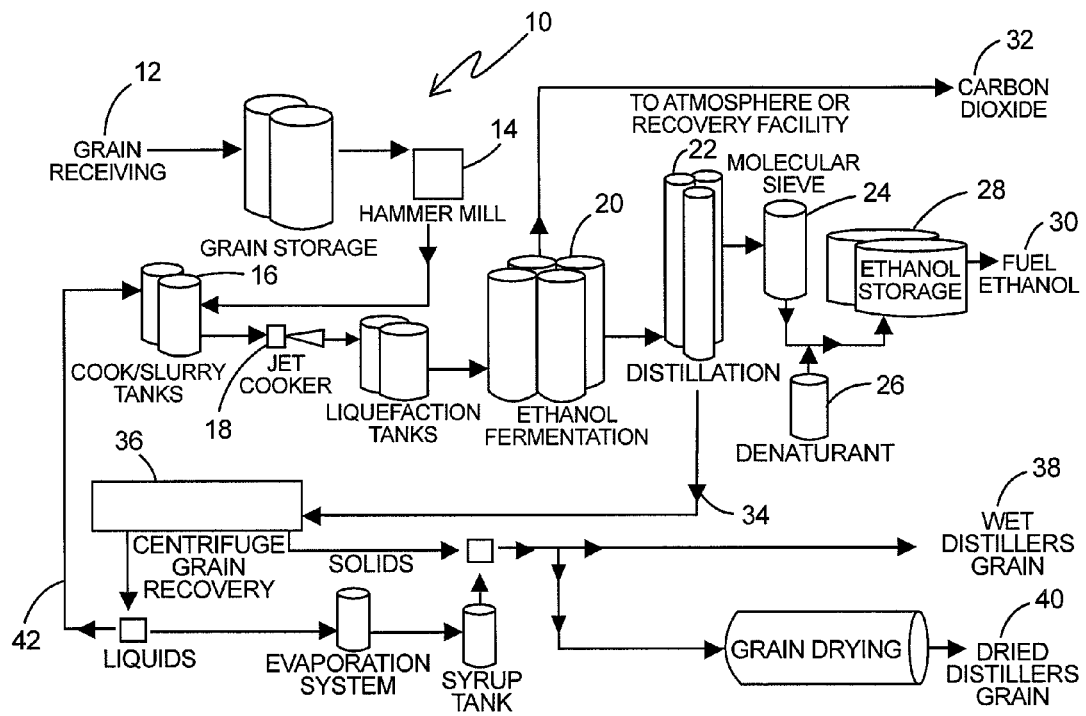
FIG. 1 is a schematic representation of a typical dry mill process for the production of ethanol from corn and other grains.

Until recently, CBNG (principally coal-bed methane (CBM)) was thought to have formed millions of years ago when the coal itself was being formed. However, recent scientific discoveries suggest that much of the gas was generated by anaerobic microbial system within the coal seams long after the initial process of coalification. This type of natural gas, referred to as secondary biogenic natural gas, relies on the active biological conversion of organic carbon from coal and terrestrial sources into methane. Most of the natural gas within the PRB is now believed to be secondary biogenic natural gas. This form of CBNG can also be found in many other large coal fields. Numerous studies have verified the presence of viable microbial communities within coal seams and other hydrocarbon reservoirs located through the United States, Canada, Australia, and China.

Renewable biogas, as stated hereinabove, principally comprising methane since the methanogens produce methane, is produced by the anaerobic digestion or fermentation of biodegradable materials such as carbonaceous compound-containing crops. The quantity of biogas that can be produced is generally limited by reaction kinetics and the size of the reactor. It is believed that coal itself, being a relatively insoluble, complex solid polymer cannot provide adequate substrate to sustain a meaningful production of biogas; however, a number of coal seams, especially those with previous CBNG deposits, contain the proper consortia of microbial populations (mostly facultative and obligate anaerobic bacteria) that are capable of producing biogenic CBNG when an external carbonaceous source is provided.

During conventional extraction of CBM, water is pumped from the coal seam to lower the hydrostatic head. Although the coal seam generally remains saturated with water, that is, the coal seam is not cleared of water, eventually the pressure decreases sufficiently that the methane starts to desorb from the coal and CBM is produced. About this time, the amount water production also begins to drop off as well.

Briefly, embodiments of the present invention include a method for using large coal fields as subsurface bioreactors for producing natural gas from terrestrial sources of biomass. The ability to create coal bed natural gas from terrestrial sources of biomass provides an opportunity to secure previously unknown sources of renewable natural gas. The technology may also be transferable to other shallow and deep terrestrial biospheres having proper biological activities, such as oil formations, shale (both coal and oil), lignite and other hydrocarbon reserves.

Plant biomass, such as alfalfa, switch grass, and corn stover, as examples, is preprocessed to remove noncellulosic constituents. The cellulose-rich product is further hydrolyzed and digested, the resulting products permitted to settle, followed by filtration. Cellulose hydrolysis and digestion may be achieved by chemical reaction using acids (generally, sulfuric acid) and/or enzymatic reaction. Settling and filtration (microfiltration) unit operations are performed prior to injection into a target coal seam, injectant concentrations being between 500 mg/L and 100,000 mg/L as total organic carbon (TOC). The solid fraction of the biomass that is separated from the injectant (liquor or soluble fraction) aboveground has commercial value and may be sold as cattle feed.

Coal seams may be screened for biogenic (methanogenic) activity as indicated by biogenic CBNG production, as well as the presence of significant population densities of methanogens and associated facultative and fermenting organisms. Coal seams might also be screened with respect to transmissivity and the likelihood of future use as a portable aquifer. Groundwater flow rate through the coal bed is an important design parameter for determining injection strategies including injectant mass loading. Expected temperatures in the methanogenically active coal seams would be in the range of 10° C. to 90° C. It is anticipated that there would be no requirement for introduction of additional bacterial species, except for microorganisms that might be carried in from an ex-situ bioreactor used for enzymatic cellulose hydrolysis, since the indigenous microorganisms are particularly well adapted to the environmental conditions within the coal seam.

Methane in biogenic natural gas is produced by a complex consortium of microorganisms including facultative, fermentative, acetogenic, and methanogenic bacteria. Facultative degradation and fermentation involve various groups of syntrophic anaerobic bacteria that together convert complex carbon substrates into low-molecular-weight organic acids like acetate ($H_3CCOOH$), hydrogen ($H_2$), and carbon dioxide ($CO_2$), which are then converted to methane and $CO_2$ by methanogenic bacteria using either acetoclastic or hydrogenotropic pathways. The word "substrate," as used herein, means the material or the substance on which an enzyme acts (i.e., the carbon source or food). Coal is not required as a substrate, but as a source of the microorganisms, since the microorganisms more readily metabolize the sugars than the coal itself.

Acetoclastic methanogenesis, which is thought to be the dominant methanogenic pathway used by the indigenous microorganisms in the PRB, occurs when certain archaea cleave acetate produced during anaerobic fermentation to yield methane ($CH_4$), and $CO_2$ according to the equation:

$$H_3CCOOH \rightarrow CH_4 + CO_2.$$

Methane can also be produced when archaea bacteria reduce carbon dioxide by using hydrogen (electrons) to yield methane and water according to:

$$4H_2 + CO_2 \rightarrow CH_4 + 2H_2O.$$

Embodiments of the present invention use biomass to optimize secondary biogenic natural gas production within the coal seam. This may be accomplished in several ways. First, cellulose and hemicellulose sugars may be used to provide an additional source of food for the microorganisms. Consequently, the microbial populations are no longer substrate limited, which allows their populations to increase. The microorganisms are the engines for methane production, and the rate of methane production may be optimized. Higher microbial populations also result in greater utilization of the available coal within the seam, further enhancing methane production. Since the process utilizes biomass, it has a significant advantage in that carbon is recycled.

As a second source of biomass, embodiments of the present CBNG generation method may be performed using various feed materials for the wet or dry mill or biomass-to-ethanol process. Wet milling of corn involves separating the grain kernel into its component parts (germ, fiber, protein and starch) prior to fermentation. The dry mill process involves grinding of the entire grain kernel into flour.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIG. 1, a schematic representation of an embodiment a typical dry mill process, 10, wherein received grain kernel, 12, corn and other grains, as examples, is ground into flour, 14, which is mixed with water to form slurry, 16, heated to liquefy portions of the slurry, 18, and fermented, 20. After distillation, 22, the ethanol is purified, 24, denatured, 26, and stored, 28, for use as fuel, 30. Carbon dioxide, 32, from fermentation process, 20, is either vented to the atmosphere or recovered. Solids and liquids, 34, remaining after ethanol distillation 22 are separated, 36, by centrifuge, to separately recover solids and liquids, which may be further processed to yield wet or dry distillers' grains, 38, 40, respectively, a portion of the liquids, 42, being returned to the fermentation process for further conversion to ethanol.

Figure 2:
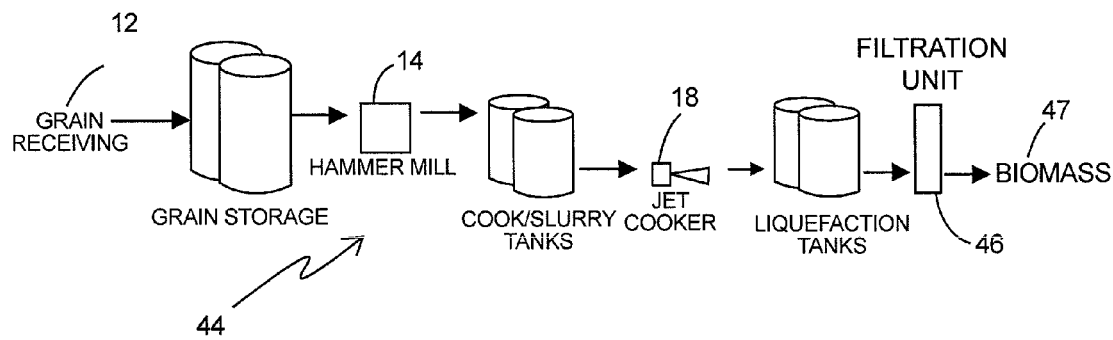
FIG. 2 is a schematic representation of an example of the manner in which the dry mill process illustrated in FIG. 1, hereof, would be modified to provide biomass input for a embodiments of the present method for production of cellulosic natural gas.

FIG. 2, illustrates that in accordance with an embodiment of the present invention, the operations, 44, associated with processing biomass material suitable for injection into methanogenically active coal seams are simplified since the coal seam serves as the fermentation reactor. After liquefaction, the biomass is filtered, 46, the liquid stream, 47, being injected into the coal seam, and the solids may be processed in a similar fashion to those of FIG. 1 to generate wet distillers grain 38 or with grain drying, dried distillers grain 40.

Figure 3:
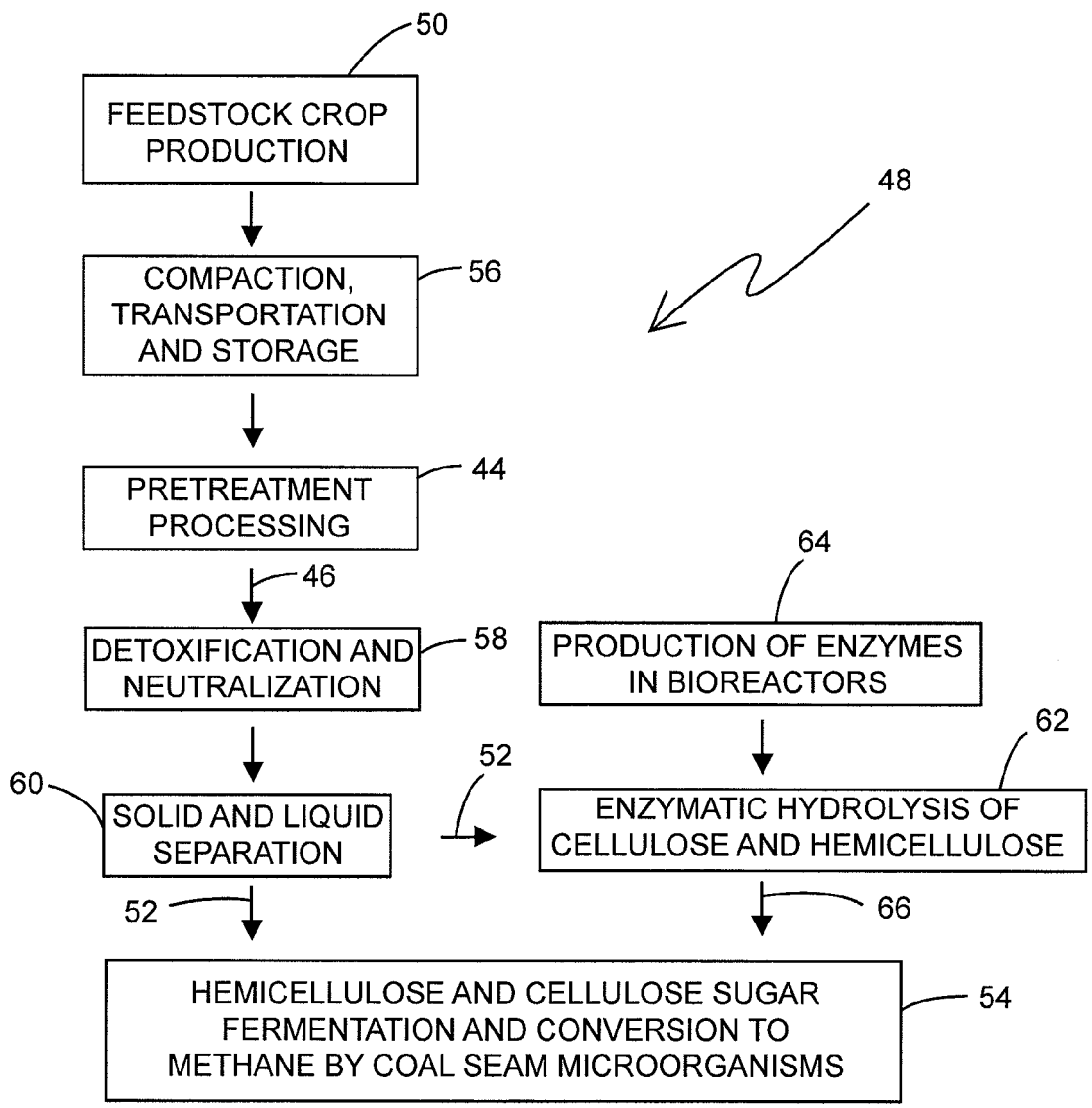
FIG. 3 is a flow chart illustrating an embodiment of the present method for production of biogenic natural gas from feedstock crops.

FIG. 3 is a flow chart showing an embodiment of the present method for the production of CBNG, 48, from feedstock crops. As stated hereinabove, perennial forage crops, 50, such as switch grass or Miscanthus, as examples, may be used to supply soluble sugars, 52, for introduction into the coal seam, 54, or for further reaction, after compaction, 56, pretreatment processing, 44, detoxification and neutralization, 58, and solid and liquid separation, 60. Atmospheric carbon dioxide is recycled by the growing crops, with the use of solar energy. The treated biomass 52 may also be converted into cellulose and hemicellulose sugars, 62, using enzymes generated, 64, in bioreactors located at or near CBNG recovery facilities, before injection, 66, into coal seams 54. In accordance with embodiments of the present invention, a solution containing the simple sugars and mineral salts may be injected into the coal seam to be transformed into natural gas by indigenous microorganisms. As microbial populations increase within the coal seam, their ability to transform the available coal-derived carbonaceous compounds into natural gas is also significantly enhanced. Produced natural gas may be recovered using the existing CBNG infrastructure.

Based on laboratory results, residence time for the biomass in the coal seam is expected to be between approximately one month and several years. Changes in methane concentration, $CH_4/CO_2$ molar ratios, and formation pressure changes with respect to time, are criteria for removing the biomass and harvesting the generated secondary methane. Mass balance analysis might be used determine injectant utilization based on stoichiometric equivalents.

Having generally described embodiments of the present invention, the following EXAMPLES provide additional details.

Example 1

Potential coal seam sites are first assessed for key microbial presence at $>10^4/L$ density; that is, the presence of facultative, fermenting, and methanogen species, as examples, by performing DNA analyses. Other relevant parameters include permeability (for distribution of the injected mineral amendments and substrate organics from biomass digestion), coal porosity (reactor volume), and water quality, for which a baseline of component concentrations may be established, including concentrations of N, P, Ca, Mg, Ni, Co, and other anions, cations, trace metals, and organic compounds.

An injection well and a circulation well are drilled, if not already available, for example, from coal bed methane recovery operations. Tracers such as bromide are injected to determine the minimum and maximum injection rates which are related to hydraulic retention time of the injectants in the coal seam. The minimum injection rate establishes the longest retention time, while the maximum injection rate establishes the shortest retention time. Multi-well patterns are implemented based on data from the site assessment and tracer studies to establish an injection/production circulation pattern that confines and maximizes the injected liquid in the reaction zone. An example of such pattern might be one injection well surrounded by 4 producing wells, although other configurations and numbers of wells may be anticipated. Well casings, necessary piping, pumps, metering systems, and the like are installed.

Feedstock for coal seam injection may include: (1) Products from aboveground biomass pretreatment and biological hydrolysis, which break down larger organic compounds into smaller injection feedstock (MW<250 Da) since hemicellulosic fractions from biomass in bioethanol plants tend to contain 5-C sugars such as xylose, which are not readily converted to ethanol by usual enzymatic catalysts, and are relegated to the waste stream; (2) Carbonaceous waste streams from existing biomass plants; and (3) products from above ground bioreactors such as in vivo enzymes such as manganese peroxidase and lignin peroxidase produced from fungi, which are capable of further catalyzing the available substrates (i.e., organic matter and coal). The feedstock is characterized before field injection to determine relevant parameters such as total organic carbon (TOC), pH, N, P, trace metals, anions, and cations. Feedstock from the above-ground biomass resources may be diluted with coal seam formation water to reach a TOC of <100,000 mg/L at the well head if the TOC in the feedstock is too high. Organic products are expected to be generated as a result of biomass degradation. The pH may be adjusted to between 5 and 9, if the feedstock is outside of this range. Macro and micro nutrients such as N, P, trace metals may be added, if necessary, to enhance microbial metabolism. Typical ranges for molar ratios of certain of the nutrients are: (1) C:N=1:3 to 1:20; and (2) C:P=1:5 to 1:200. Typical ranges for Ca and Mg are between 1 and 100 mg/L, while those for Ni and Co are between 2 and 200 µg/L/. It should be mentioned that although the indigenous formation water contains a small amount of TOC, the majority of the TOC is supplied from aboveground biomass sources, in accordance with embodiments of the present invention.

Following injection into the circulation wells, the wells are sampled and monitored for feedstock concentration, organic acids and pH. A TOC within the range of 10 mg/L to 10,000 mg/L may be maintained in the formation water by controlling the injection. Product gas will follow routes having the highest permeability, for example, toward producing and injecting wells. However, pumping is expected to enhance the gas recovery. Product gas will be sampled from the annulus and monitored for composition, such as for methane, propane butane, carbon dioxide, nitrogen, and oxygen, as examples. Circulation rates, achieved by pumping, may be adjusted, and important nutrients that fall below their chosen ranges may be added, as needed to maximize $CH_4$ production and its content in the produced gas.

Although produced water is pumped from CBNG formations, in accordance with embodiments of the present invention, such pumped water is used for establishing circulation through the coal seam. The recovered formation water is amended with substrates (e.g. sugars), such that it can be injected at another location. In this way the water is recirculated through the coal seam. As it flows from the point of injection to the point of recovery the microorganisms will convert the dissolved sugars to natural gas. If the addition of substrates is properly augmented, the concentration of the sugars at the point of recovery should be low.

Example 2

Figure 4:
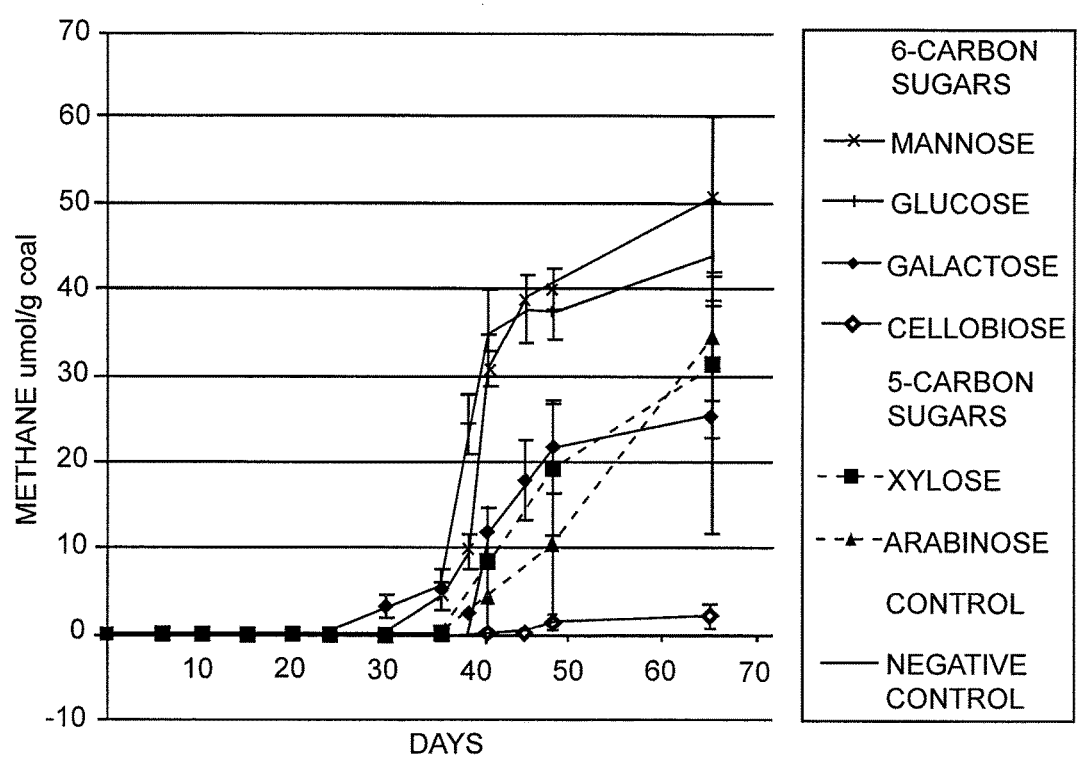
FIG. 4 is a graph of laboratory data showing the biogenic production of methane from several biomass-derived substrates including 5- and 6-carbon sugars using microorganisms indigenous to the coal seam.

FIG. 4 is a graph of laboratory data showing the biogenic production of methane from several biomass-derived substrates including 5- and 6-carbon sugars using microorganisms indigenous to the coal seam. The inocula were microorganisms obtained from a coal sample from Bridle Bit Ranch FED 41-18 well located in NE 18 Township 42, North Range 72 West (AIP 49-005-60373) in the Wyodak formation. The depth of the well was between 1026 feet and 1053 feet and the extraction date was 15 Nov. 2008. The sample was rinsed with sterile deionized water and vacuum sealed, then stored under nitrogen gas ($N_2$) conditions at 4° C. until utilized. The coal was never directly exposed to the atmosphere. Anaerobic batch reaction cultures were prepared to assess the microbial dynamics occurring within serum bottles at ambient temperature (~22° C.). Methane production, pH and organic acid production were recorded. The pH was neutrally buffered, but actual values were between 6.0 and 7.0. Common hexose and pentose sugars derived from plant hemicelluloses were used. The hexoses: glucose, mannose, galactose, and cellobiose; and the pentoses: xylose and arabinose, were used as substrates. All cultures were prepared in 160 ml serum bottles under anaerobic conditions. The growing medium used was a methanogenic medium, which included trace metals, minerals, and vitamins necessary for anaerobic methanogenic growth. A rezasurin (visible) indicator was used to indicate oxygen contamination, and a phosphate buffer was also present. Each serum bottle was filled with 10 g of crushed coal, 50 ml of medium, and 5 milliMolar concentration of substrate.

The vertical black line in FIG. 4 shows the confidence interval (±95%) associated with the data. The negative control was filled with 10 g of inocula coal, 50 ml of the medium, and no substrate. From FIG. 4 it is seen that the initial 35 days represents the lag time in which the microorganisms are adapting to their new environment (i.e., sugar in place of coal as the food source).

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for generating methane gas, comprising the steps of:
   determining microbial presence, permeability and volume of a chosen coal seam;
   injecting tracers into the chosen coal seam to determine the retention time of the tracers in the coal seam;
   providing at least one injection well and at least one circulation well effective for generating an injection rate related to the retention time;
   injecting a solution having a chosen concentration of biomass into the coal seam;
   digesting or fermenting a chosen quantity of the biomass injected into the coal seam by microbial action to produce methane gas from the biomass; and
   extracting the methane gas from the coal seam,
   wherein the biomass is chosen from a cellulose carbonaceous waste stream from a biomass plant, a hemicellulose carbonaceous waste stream from a biomass plant, and a hemicellulose containing waste stream from a bioethanol facility.

2. The method of claim 1, wherein said step of injecting a solution of biomass into the coal seam comprises the steps of: producing water from the coal seam; mixing the produced water with a solution of biomass to form a solution having a chosen concentration of biomass; and injecting the solution having the chosen concentration of biomass into the coal seam at a selected rate.

3. The method of claim 2, further comprising the step of maintaining total organic carbon in the coal seam at a chosen level.

4. The method of claim 3, wherein said step of maintaining total organic carbon at a chosen level is achieved by controlling the selected rate of injection of the solution having a chosen concentration of biomass.

5. The method of claim 3, wherein said step of maintaining total organic carbon at a chosen level is achieved by controlling the chosen concentration of biomass in the solution having a chosen concentration of biomass.

6. The method of claim 2, wherein said step of digesting or fermenting a chosen quantity of the biomass by microbial action in the coal seam is achieved by controlling the selected rate of injection of the solution having a chosen concentration of biomass.

7. The method of claim 1, wherein the biomass is a hemicellulose containing waste product from bioethanol production.

8. The method of claim 7, wherein the biomass comprises 5-carbon and 6-carbon sugars.

9. The method of claim 1, wherein the biomass is a cellulose or hemicellulose carbonaceous waste from a biomass treatment plant.

10. The method of claim 1, further comprising the step of injecting enzymes into the coal seam.

11. A method for generating methane gas, comprising the steps of:
  injecting a solution having a chosen concentration of biomass into a methanogenically active coal bed;
  digesting or fermenting a chosen quantity of the biomass injected into the coal bed by anaerobic bacteria to produce methane gas from the biomass; and
  extracting the methane gas from the coal bed,
  wherein the biomass is chosen from a cellulose carbonaceous waste stream from a biomass plant, a hemicellulose carbonaceous waste stream from a biomass plant, and a hemicellulose containing waste stream from a bioethanol facility.

12. The method of claim 11, wherein said step of injecting a solution having a chosen concentration of biomass into the coal bed comprises the steps of: producing water from the coal bed; mixing the produced water with a solution of biomass; and injecting the mixed produced water and biomass into the coal bed at a selected rate.

13. The method of claim 12, further comprising the step of maintaining total organic carbon in the coal bed at a chosen level.

14. The method of claim 13, wherein said step of maintaining total organic carbon at a chosen level is achieved by controlling the selected rate of injection of the solution having a chosen concentration of biomass.

15. The method of claim 13, wherein said step of maintaining total organic carbon at a chosen level is achieved by controlling the chosen concentration of biomass in the solution having a chosen concentration of biomass.

16. The method of claim 12, wherein said step of digesting or fermenting a chosen quantity of the biomass by microbial action in the coal bed is achieved by controlling the selected rate of injection of the solution having a chosen concentration of biomass.

17. The method of claim 11, wherein the biomass is a hemicellulose containing waste product from bioethanol production.

18. The method of claim 17, wherein the biomass comprises 5-carbon and 6-carbon sugars.

19. The method of claim 17, further comprising the step of injecting enzymes into the coal bed.

20. The method of claim 11, wherein the biomass is a cellulose or hemicellulose carbonaceous waste from a biomass treatment plant.

21. A method for generating coal bed methane gas, comprising the steps of:
  removing a portion of the water from a methane coal bed;
  extracting desorbed methane gas;
  injecting a solution having a chosen concentration of biomass into the coal bed;
  digesting or fermenting a chosen quantity of the biomass injected into the coal bed by anaerobic bacteria to produce methane gas; and
  extracting the methane gas from the coal bed,
  wherein the biomass is chosen from a cellulose carbonaceous waste stream from a biomass plant, a hemicellulose carbonaceous waste stream from a biomass plant, and a hemicellulose containing waste stream from a bioethanol facility.

22. The method of claim 21, wherein said step of injecting a solution having a chosen concentration of biomass into the coal bed comprises the steps of: producing water from the coal bed; mixing the produced water with a solution of biomass; and injecting the mixed produced water and biomass into the coal bed at a selected rate.

23. The method of claim 22, further comprising the step of maintaining total organic carbon in the coal bed at a chosen level.

24. The method of claim 23, wherein said step of maintaining total organic carbon at a chosen level is achieved by controlling the selected rate of injection of the solution having a chosen concentration of biomass.

25. The method of claim 23, wherein said step of maintaining total organic carbon at a chosen level is achieved by controlling the chosen concentration of biomass in the solution having a chosen concentration of biomass.

26. The method of claim 22, wherein said step of digesting or fermenting a chosen quantity of the biomass by microbial action in the coal seam is achieved by controlling the selected rate of injection of the solution having a chosen concentration of biomass.

27. The method of claim 21, wherein the biomass is a hemicellulose containing waste product from bioethanol production.

28. The method of claim 27, wherein the biomass comprises 5-carbon and 6-carbon sugars.

29. The method of claim 21, wherein the biodegradable biomass is a cellulose or hemicellulose carbonaceous waste from a biomass treatment plant.

30. The method of claim 21, further comprising the step of injecting enzymes into the coal bed.

* * * * *